United States Patent [19]

Fearon et al.

[11] Patent Number: 4,659,502
[45] Date of Patent: Apr. 21, 1987

[54] ETHANE DERIVATIVES

[75] Inventors: Julie E. Fearon, Hull; Wendy E. Smith, Lincoln; George W. Gray, Cottingham; David Lacey; Kenneth J. Toyne, both of Hull, all of Great Britain; Georg Weber, Erzhausen, Fed. Rep. of Germany

[73] Assignee: Merck Patent Gesellschaft mit Beschränkter Haftung, Darmstadt, Fed. Rep. of Germany

[21] Appl. No.: 691,980

[22] Filed: Jan. 17, 1985

[30] Foreign Application Priority Data

Jan. 17, 1984 [DE] Fed. Rep. of Germany ....... 3401320

[51] Int. Cl.$^4$ .................. G02F 1/13; C09K 19/34; C09K 19/32; C09K 19/30
[52] U.S. Cl. .................. 252/299.61; 252/299.5; 549/22; 549/370; 252/299.62; 549/372; 549/373; 252/299.63; 252/299.66; 252/299.6; 350/350 R; 350/350 S; 558/414; 558/415; 558/416; 558/417; 558/419; 558/420; 558/421; 558/425; 558/426; 544/224; 544/238; 544/239; 544/241; 544/295; 544/296; 544/309; 544/310; 544/335; 544/311; 544/312; 544/316; 544/317; 544/319; 544/334; 549/21
[58] Field of Search ............ 252/299.5, 299.6, 299.61, 252/299.62, 299.63, 299.66; 350/350 R, 350 S; 260/465 C, 465 D, 465 R, 465 F, 465 G, 465 H; 544/335, 315, 242, 298, 239, 241, 224, 238, 295, 311, 296, 310, 312, 309, 316, 317, 319, 334; 549/21, 22, 373, 370, 372; 558/414, 415, 416, 417, 425, 419, 430, 421, 426

[56] References Cited

U.S. PATENT DOCUMENTS

| 4,035,056 | 7/1977 | Coates et al. | 252/299.66 |
|---|---|---|---|
| 4,261,651 | 4/1981 | Gray et al. | 252/299.63 |
| 4,393,258 | 7/1983 | Sato et al. | 252/299.63 |
| 4,400,293 | 8/1983 | Romer et al. | 252/299.63 |
| 4,419,263 | 12/1983 | Praefcke et al. | 252/299.63 |
| 4,439,015 | 3/1984 | Rich et al. | 252/299.63 |
| 4,455,443 | 6/1984 | Takatsu et al. | 252/299.63 |
| 4,460,770 | 7/1984 | Petrzilka et al. | 252/299.65 |
| 4,472,592 | 9/1984 | Takatsu et al. | 252/299.63 |
| 4,480,117 | 10/1984 | Takatsu et al. | 252/299.63 |
| 4,510,069 | 4/1985 | Eidenschime et al. | 252/299.61 |
| 4,512,646 | 4/1985 | Andrews et al. | 252/299.61 |
| 4,514,044 | 4/1985 | Gunjima | 252/299.63 |
| 4,514,317 | 4/1985 | Tuong et al. | 252/299.62 |
| 4,526,704 | 7/1985 | Petrzilka et al. | 252/299.64 |
| 4,550,981 | 11/1985 | Petrzilka et al. | 252/299.63 |
| 4,551,280 | 11/1985 | Sasaki et al. | 252/299.63 |
| 4,556,745 | 12/1985 | Carr et al. | 252/299.63 |
| 4,558,151 | 12/1985 | Takatsu et al. | 252/299.63 |
| 4,583,826 | 4/1986 | Petrzilka et al. | 252/299.63 |

FOREIGN PATENT DOCUMENTS

| 84194 | 7/1983 | European Pat. Off. | 252/299.63 |
|---|---|---|---|
| 107116 | 5/1984 | European Pat. Off. | 252/299.63 |
| 129177 | 12/1984 | European Pat. Off. | 252/299.63 |
| 149238 | 7/1985 | European Pat. Off. | 252/299.61 |

(List continued on next page.)

OTHER PUBLICATIONS

Tinh, N. et al., Mol. Cryst. Liq. Cryst., vol. 56, No. 10 (Letters), pp. 323-330 (1980).

Primary Examiner—Teddy S. Gron
Attorney, Agent, or Firm—Millen & White

[57] ABSTRACT

Ethane derivatives of the formula I

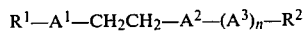

$$R^1-A^1-CH_2CH_2-A^2-(A^3)_n-R^2 \qquad I$$

wherein
$R^1$ is H, an alkyl group with 1-12 C atoms, in which one or two non adjacent $CH_2$ groups can also be replaced by O atoms and/or CO groups and/or —O—CO— groups and/or —CO—O groups, F, Cl, Br or $R^3-A^4-Z^1$—,
$R^2$ is —CN or —$Z^2-A^4$—CN,
$A^1$ is —A—, —A—$A^5$— or —$A^5$—A—,
$A^2$ is an 1,4-phenylene group which is unsubstituted or substituted by one or two F and/or Cl atoms and/or $CH_3$ groups and/or CN groups and in which one or two CH groups can also be replaced by N atoms,
A is a 1,4-cyclohexylene group, in which one or two non adjacent $CH_2$ groups can also be replaced by O atoms, or is a 1,3-dithiane-2,5-diyl group or 1,4-bicyclo(2,2,2)-octylene group,
$A^3$, $A_4$ are each a 1,4-cyclohexylene group, in which one or two non adjacent $CH_2$ groups can also be replaced by O atoms, or are each a 1,3-dithiane-2,5-diyl group, and
$A^5$ or a 1,4-phenylene group which is unsubstituted or substituted by one or two F and/or Cl atoms and/or $CH_3$ groups and/or CN groups, and in which one or two CH groups can also be replaced by N atoms,
n is 0 or 1,
$Z^1$ is —CO—O—, —O—CO—, —$CH_2CH_2$—, —$CH_2O$—, —$OCH_2$ or a single bond,
$Z^2$ is —$CH_2CH_2$—, —$CH_2O$—, —$OCH_2$—, —O—CO— or a single bond and
$R^3$ is H or an alkyl group with 1-12 C atoms, in which one or two non adjacent $CH_2$ groups can also be replaced by O atoms and/or CO groups and/or —CO—O— groups and/or —O—CO— groups,
with the proviso that
(a) if $A^2=A^3=$1,4-phenylene (n=1) and/or if $R^1-A^1=$p-(trans-4-alkylcyclohexyl)-phenyl, at least one of the groups $A^2$ and/or $A^3$ is laterally substituted, and
(b) if $A^1=A$ and/or $R^1-A^1=$trans-4-(trans-4-alkylcyclohexyl)-cyclohexyl, n is 1, can be used as components of liquid crystal phases.

20 Claims, No Drawings

FOREIGN PATENT DOCUMENTS

| | | | |
|---|---|---|---|
| 3237367 | 4/1983 | Fed. Rep. of Germany | 252/299.63 |
| 3317597 | 11/1984 | Fed. Rep. of Germany | 252/299.63 |
| 3405914 | 8/1985 | Fed. Rep. of Germany | 252/299.61 |
| 3404116 | 8/1985 | Fed. Rep. of Germany | 252/299.61 |
| 3410733 | 10/1985 | Fed. Rep. of Germany | 252/299.61 |
| 3411571 | 10/1985 | Fed. Rep. of Germany | 252/299.61 |
| 3410734 | 10/1985 | Fed. Rep. of Germany | 252/299.63 |
| WO85/04874 | 11/1985 | PCT Int'l App. | 252/299.63 |
| 2078727 | 1/1982 | United Kingdom | 252/299.6 |
| 2052169 | 8/1982 | United Kingdom | 252/299.6 |
| 2121406 | 12/1983 | United Kingdom | 252/299.6 |
| 2134110 | 8/1984 | United Kingdom | 252/299.6 |

ETHANE DERIVATIVES

BACKGROUND OF THE INVENTION

This invention relates to ethane derivatives useful in liquid crystal applications.

SUMMARY OF THE INVENTION

It is an object of this invention to provide new compounds useful as liquid crystals.

Upon further study of the specification and appended claims, further objects and advantages of this invention will become apparent to those skilled in the art.

These objects have been achieved by providing ethane derivatives of the formula I $$R^1-A^1-CH_2CH_2-A^2-(A^3)_n-R^2 \qquad \text{I}$$

wherein
- $R^1$ is H; an alkyl group with 1-12 C atoms, in which one or two non adjacent $CH_2$ groups can also be replaced by O atoms and/or CO groups and/or —O—CO— groups and/or —CO—O— groups; F; Cl; Br; or $R^3$-$A^4$—$Z^1$,
- $R^2$ is —CN or —$Z^2$—$A^4$—CN,
- $A^1$ is —A—, —A—$A^5$— or —$A^5$—A—,
- $A^2$ is a 1,4-phenylene group which is unsubstituted or substituted by one or two F and/or Cl atoms and/or $CH_3$ groups and/or CN groups and in which one or two CH groups can also be replaced by N atoms,
- A is a 1,4-cyclohexylene group, in which one or two non adjacent $CH_2$ groups can also be replaced by O atoms, or is a 1,3-dithiane-2,5-diyl group or 1,4-bicyclo(2,2,2)-octylene group,
- $A^3$, are independently each a 1,4-cyclohexylene group,
- $A^4$ in which one or two non adjacent $CH_2$ groups can and also be replaced by O atoms, or are each a
- $A^5$ 1,3-dithiane-2,5-diyl group, or a 1,4-phenylene group which is unsubstituted or substituted by one or two F and/or Cl atoms and/or $CH_3$ groups and/or CN groups, and in which one or two CH groups can also be replaced by N atoms,
- n is 0 or 1,
- $Z^1$ is —CO—O—, —O—CO—, —$CH_2CH_2$—, —$CH_2O$—, —$OCH_2$— or a single bond,
- $Z^2$ is —$CH_2CH_2$—, —$CH_2O$—, —$OCH_2$—, —O—CO— or a single bond and
- $R^3$ is H or an alkyl group with 1-12 C atoms, in which one or two non adjacent $CH_2$ groups can also be replaced by O atoms and/or CO groups and/or —CO—O— groups and/or —O—CO— groups, with the proviso that
- (a) if $A^2=A^3=$1,4-phenylene (n=1) and/or if $R^1-A^1=$p-(trans-4-alkylcyclohexyl)-phenyl, at least one of the groups $A^2$ and/or $A^3$ is laterally substituted, and
- (b) if $A^1=A$ and/or $R^1-A^1=$trans-4-(trans-4-alkylcyclohexyl)-cyclohexyl, n is 1.

For simplicity, in the following text Phe is a 1,4-phenylene group, Cy is a 1,4-cyclohexylene group, Dio is a 1,3-dioxane-2,4-diyl group, Dit is a 1,3-dithiane-2,5-diyl group, Bi is a bicyclo(2,2,2)octylene group, Pyn is a pyridazine-3,6-diyl group and Pyr is a pyrimidine-2,5-diyl group, it being possible for these groups, in particular the 1,4-phenylene group, to be unsubstituted or substituted by one or two F and/or Cl atoms and/or $CH_3$ groups and/or CN groups.

DETAILED DISCUSSION

The compounds of the formula I can be used as components of liquid crystal phases, in particular for displays based on the principle of the twisted cell, the guest-host effect, the effect of deformation of aligned phases or the effect of dynamic scattering.

The invention was based on the object of discovering new stable liquid crystal or mesogenic compounds which are suitable as components of liquid crystal phases.

It has been found that the compounds of the formula I are outstandingly suitable as components of liquid crystal dielectrics. In particular, liquid crystal phases with small $k_{33}/k_{11}$ values, a very low viscosity and a comparatively low optical anisotropy can be prepared with the aid of these compounds. Some of the compounds of the formula I are furthermore suitable as components of smectic phases (for example for the memory effect).

In addition, by providing the compounds of the formula I, the range of liquid crystal substances which are suitable, from various technological viewpoints, for the preparation of nematic mixtures is quite generally considerably extended.

The compounds of the formula I have a wide range of application. Depending on the choice of the substituents, these compounds can be used as base materials from which liquid crystal dielectrics are predominantly composed; however, compounds of the formula I can also be added to liquid crystal base materials from other classes of compounds, for example in order to reduce the dielectric and/or optical anisotropy of such a dielectric The compounds of the formula I are furthermore suitable as intermediates for the preparation of other substances which can be used as constituents of liquid crystal dielectrics.

The compounds of the formula I are colorless in the pure state and form liquid crystal mesophases in a temperature range which is advantageously located for electrooptical use. They are very stable towards chemicals, changes in temperature and light.

The invention thus relates to the compounds of the formula I and to a process for their preparation, characterised in that a corresponding carboxylic acid amide is dehydrated or a corresponding carboxylic acid halide is reacted with sulfamide, or in that a corresponding bromine or chlorine compound is reacted with a cyanide.

The invention furthermore relates to the use of the compounds of the formula I as components of liquid crystal phases. The invention moreover relates to liquid crystal phases containing at least one compound of the formula I, and to liquid crystal display elements, in particular electrooptical display elements, containing such phases.

$R^1$, $R^2$, $R^3$, $A^1$, $A^2$, $A^3$, $A^4$, $A^5$, A, $Z^1$ and $Z^2$ above and below have the meaning given, unless expressly indicated otherwise.

The compounds of the formula I accordingly include compounds of the sub-formulae Ib to Id (with in each case three rings), If to Ih (with four rings) and Ii and Ij (with five rings):

$$R^1-A-A^5-CH_2CH_2-A^2-CN \qquad \text{Ib}$$

$$R^1-A^5-A-CH_2CH_2-A^2-CN \qquad \text{Ic}$$

R¹—A—CH₂CH₂—A²—A³—CN  Id

R¹—A—CH₂CH₂—A²—A³—Z²—A⁴—CN  If

R¹—A—A⁵—CH₂CH₂—A²—A³—CN  Ig

R¹—A⁵—A—CH₂CH₂—A²—A³—CN  Ih

R¹—A—A⁵—CH₂CH₂—A²—A³—Z²—A⁴—CN  Ii

R¹—A⁵—A—CH₂CH₂—A²—A³—Z²—A⁴—CN  Ij

The preferred compounds of the sub-formula Ib include those of the sub-formulae Iba to Ibc:

R¹—Cy—Phe—CH₂CH₂—PhX—CN  Iba

R¹—Dio—Phe—CH₂CH₂—PhX—CN  Ibb

R¹—Dit—Phe—CH₂CH₂—PhX—CN  Ibc

Among these, those of the sub-formula Iba are particularly preferred.

In the formulae above and below, PhX is a 1,4-phenylene group which is substituted by one or two F and/or Cl atoms and/or CH₃ groups and/or CN groups.

The preferred compounds of the sub-formula Id include those of the sub-formulae Ida to Idi:

R¹—A—CH₂CH₂—Pyr—Phe—CN  Ida

R¹—A—CH₂CH₂—Pyr—PhX—CN  Idb

R¹—A—CH₂CH₂—PhX—Phe—CN  Idc

R¹—A—CH₂CH₂—Phe—PhX—CN  Ide

R¹—A—CH₂CH₂—PhX—Cy—CN  Idf

R¹—A—CH₂CH₂—Pyn—Phe—CN  Idg

R¹—A—CH₂CH₂—Pyn—Cy—CN  Idh

R¹—A—CH₂CH₂—Phe—Cy—CN  Idi

Of these, those of the sub-formulae Idc to Idf, in particular Idb to Ide, are particularly preferred. Idi is also preferred. Compounds of the formulae Idc and Ide wherein A is trans-1,4-cyclohexylene and R¹ is alkyl with 1-12 C atoms are particularly preferred.

The preferred compounds of the sub-formula If include those of the sub-formulae Ifa to Ife:

R¹—A—CH₂CH₂—PhX—Phe—Cy—CN  Ifa

R¹—A—CH₂CH₂—Phe—PhX—Cy—CN  Ifb

R¹—A—CH₂CH₂—Pyr—Phe—Cy—CN  Ifc

R¹—A—CH₂CH₂—Pyn—Phe—Cy—CN  Ifd

R¹—A—CH₂CH₂—Phe—Phe—Cy—CN  Ife

The preferred compounds of the sub-formula Ig include those of the sub-formulae Iga to Igh:

R¹—A—Phe—CH₂CH₂—PhX—Phe—CN  Iga

R¹—A—Phe—CH₂CH₂—Phe—PhX—CN  Igb

R¹—A—Phe—CH₂CH₂—Phe—PhX—CN  Igc

R¹—A—Phe—CH₂CH₂—PhX—Cy—CN  Igd

R¹—A—PhX—CH₂CH₂—Phe—Cy—CN  Ige

R¹—A—Phe—CH₂CH₂—Pyr—Phe—CN  Igf

R¹—A—Phe—CH₂CH₂—Pyn—Phe—CN  Igh

Of these, those of the sub-formulae Iga to Igc are particularly preferred.

The preferred compounds of the sub-formula Ih include those of the sub-formulae Iha to Ihf:

R¹—Cy—A—CH₂CH₂—PhX—Phe—CN  Iha

R¹—Cy—A—CH₂CH₂—Phe—PhX—CN  Ihb

R¹—Cy—A—CH₂CH₂—PhX—Cy—CN  Ihc

R¹—Cy—A—CH₂CH₂—Pyr—Phe—CN  Ihd

R¹—Cy—A—CH₂CH₂—Pyn—Phe—CN  Ihe

R¹—Cy—A—CH₂CH₂—Phe—Cy—CN  Ihf

Of these, those of the sub-formulae Iha and Ihb are particularly preferred. Ihf is also preferred.

In the compounds of the formulae above and below, R¹ and R³ are preferably alkyl, and furthermore alkoxy or another oxaalkyl group. (A³)ₙ—R² is preferably —A³—CN or —A³—Z²—A⁴—CN, in particular —A³—CN.

A¹ is preferably —A— or —A—A⁵.

A is preferably Cy, Dio or Dit, in particular Cy.

A² is preferably Phe, PhX, Pyr, Pyn or a pyridine-2,5-diyl group, in particular Phe or PhX. Phx is preferably a 1,4-phenylene group which is substituted in the 2- or 3-position by F, Cl or CH₃, in particular F or CH₃.

A³, A⁴ and A⁵ are preferably Phe, PhX, Cy or Dio, and furthermore preferably Dit, Pyr or Pyn.

A³ and A⁴ are preferably Phe and Cy.

The compound of the formula I preferably contains not more than one of the radicals Dio, Dit, PhX, Pyr or Pyn, or related rings.

Z¹ and Z² are preferably single bonds, or, secondly, preferably —CO—O—, —CO—O— or —CH₂—CH₂— groups.

If R¹ or R³ is alkyl in which one ("alkoxy" or "oxaalkyl") or two ("alkoxyalkoxy" or "dioxaalkyl") non adjacent CH₂ groups can be replaced by O atoms, they can be straight-chain or branched. Preferably, they are straight-chain and have 2, 3, 4, 5, 6 or 7 C atoms, and accordingly are preferably ethyl propyl, butyl, pentyl, hexyl, heptyl, ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, or furthermore methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9 -oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxahepthyl.

Compounds of the formula I with branched end group substituents R¹ or R³ may occasionally be of importance because of a better solubility in the usual liquid crystal base materials, but in particular as chiral doping substances, if they are optically active. Chiral compounds of the formula I are furthermore suitable for the preparation of smectic S$_c$* phases. Branched groups of this type as a rule contain not more than one chain-branching. Preferred branched radicals $R^1$ and $R^3$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2methylpropoxy, 2-methylbutoxy, 3-methylbutoxy, 2-methylpentoxy, 3-methylpentoxy, 2-ethylhexoxy, 1-methylhexoxy, 1-methylheptoxy, 2-octyloxy, 2-oxa-3-methylbutyl and 3-oxa-4-methylpentyl.

Of the compounds of the formula I, those in which at least one of the radicals contained therein has one of the preferred meanings given are preferred.

Compounds of the formula I wherein $A^2$ or $A^3$, in particular $A^3$, is a 1,4-phenylene group which is substituted by one or two F and/or Cl atoms and/or $CH_3$ groups and/or CN groups, in particular by one or two F atoms or $CH_3$ groups, and compounds of the formula I wherein A is a 1,4-cyclohexylene group, are also preferred.

Of the compounds of the formula I, those stereoisomers in which the cycloaliphatic radicals (for example Cy, Dio and Dit) are trans-1,4disubstituted are preferred.

Those of the abovementioned formulae which contain one or more of the groups Dio, Dit and/or Pyr and/or related rings in each case include the two possible 2,5-position isomers as well as the two possible position isomers of the other rings.

Particularly preferred compounds of the formula I and of the above sub-formulae are those wherein $R^1$ is a straight-chain alkyl group or alkoxy group with in each case 1 to 10 C atoms.

Compounds of the formula I wherein at least one of the groups $A^2$, $A^3$, $A^4$ and $A^5$ is Pyr, Pyn or Pyrazine-2,5-diyl, in particular Pyr (that is to say 1,4-phenylene, wherein two CH groups are replaced by N atoms) are also preferred.

The compounds of the formula I are prepared by methods which are known per se, such as those described in the literature (for example in the standard works, such as Houben-Weyl, Methoden der Organischen Chemie (Methods of Organic chemistry), Georg Thieme-Verlag, Stuttgart), and in particular under reaction conditions which are known and suitable for the reactions mentioned. Variants which are known per se and are not mentioned in more detail here can also be used.

The expert can find corresponding synthesis methods by routine methods from the prior art (for example German Offenlegungsschrift No. 2,429,093; U.S. Pat. Nos. 3,826,757; 4,065,489; 4,136,053; 4,137,192; 4,130,502; 4,154,697 and 4,293,434, in respect of compounds with 1,4-cyclohexylene and 1,4-phenylene groups: U.S. Pat. No. 4,062,798, in respect of compounds with pyrimidine-2,5-diyl groups; U.S. Pat. No. 4,419,262, in respect of compounds with pyridazine-3,6-diyl groups; Japanese Published Application No. 58-43,961, in respect of compounds with pyrazine-2,5-diyl groups; German Offenlegungsschrift No. 3,227,916 and U.S. Pat. No. 4,344,856, in respect of compounds with 1,3-dioxane-2,5-diyl groups; East German Pat. No. 160,061, in respect of compounds with 1,3-dithiane-2,5-diyl groups; U.S. Pat. Nos. 4,261,652 and 4,219,256, in respect of compounds with 1,4-bicyclo(2,2,2)octylene groups; U.S. Pat. No. 4,432,885, in respect to compounds with decahydronaphthalene-2,6-diyl groups; U.S. Pat. No. 4,386,007, in respect of compounds with 1,2,3,4-tetrahydronaphthalene-2,6-diyl groups; German Offenlegungsschrift No. 3,208,089; U.S. Pat. Nos. 4,419,264 and 4,415,476 and European Published Application No. 84,194, in respect of laterally substituted compounds; and U.S. Pat. No. 4,439,015, in respect of compounds with $-CH_2CH_2-$ bridge members).

If desired, the starting substances can also be formed in situ, in a manner such that they are not isolated from the reaction mixture but are immediately further reacted to give the compounds of the formula I.

The compounds of the formula I can thus be prepared by dehydrating a corresponding carboxylic acid amide or reacting a corresponding carboxylic acid halide with sulfamide. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ and $COCl_2$, and furthermore $P_2O_5$, $P_2S_5AlCl_3$ (for example as a double compound with NaCl) and aromatic sulfonic acids and sulfonic acid halides. The dehydration can be carried out in the presence or absence of an inert solvent at temperatures between about 0° and 150°; examples of possible solvents are bases, such as pyridine or triethylamine, aromatic hydrocarbons, such as benzene, toluene or xylene, or amides, such as dimethylformamide.

To prepare the ethane derivatives of the formula I, it is also possible to react corresponding acid halides, preferably the chlorides, with sulfamide, advantageously in an inert solvent, such as tetramethylene sulfone, at temperatures between about 80° and 140°, preferably at 120°. After customary working up, the nitriles can be isolated directly.

For the starting substances, the expert can find corresponding synthesis methods from the prior art. Benzoic acid halides (corresponding to formula I, wherein $-A^2-(A^3)_n-R^2=-Phe-COHalogen$, $-A^2-Phe-COHalogen$, $-A^3-Z^2-Phe-COHalogen$, $-PhX-COHalogen$, $-A^2PhX-COHalogen$ or $-A^3-Z^2-PhX-COHalogen$) can be prepared, for example, from corresponding benzene derivatives (for example those which contain an H atom instead of the COHalogen radical) by reaction with oxalyl halide, preferably oxalyl chloride, under Friedel-Crafts conditions (British Patent Application No. 8,206,265).

Corresponding cyclohexanecarboxylic acid derivatives (for example acid halides or esters; corresponding to formula I, wherein $-A^2-(A^3)_n-R^2$ is, for example, $-A^3-Cy-CN$) are accessible, for example, from halogen compounds, preferably bromides or chlorides) corresponding to formula I, wherein $-A^2-(A^3)_n-R^2$ is $-A^3-halogen$, by Grignard reaction with 4-(4,5-dihydro-4,4-dimethyl-2-oxazolyl)-cyclohexanone, detachment of water, with simultaneous removal of the oxazolyl protective group, by boiling with ethanolic $H_2SO_4$, hydrogenation of the double bond and, if appropriate, conversion of the ethyl ester into the desired acid derivative by methods which are known from the literature.

To prepare ethane derivatives of the formula I, it is also possible to react corresponding chlorine or bromine compounds with a cyanide by methods which are known from the literature, advantageously with a metal cyanide, such as NaCN, KCN or $Cu_2(CN)_2$, for example in the presence of pyridine in an inert solvent, such as dimethylformamide or N-methylpyrrolidone, at temperatures between 20° and 200°.

For the chlorine or bromine compounds, the expert can find appropriate synthesis methods from the prior art. For example, these compounds are accessible by halogenation of the benzene derivatives described above. Similarly, all of the variants discussed above can be prepared from readily prepared starting materials, e.g., when other hetero rings are involved.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

The liquid crystal phases according to the invention comprise 2 to 15, preferably 3 to 12, components, at least one of which is a compound of the formula I. The other constituents are preferably chosen from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-dioxanes, phenyl- or cyclohexyl-1,3-dithianes, 1,2-diphenylethanes, 1,2-dicyclohexylethanes, 1-cyclohexyl-2-phenylethanes, optionally halogenated stilbenes, benzyl phenyl ethers, tolanes and substituted cinnamic acids.

The most important compounds which are possible constituents of liquid crystal phases of this type can be characterized by the formula II

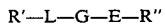   R'—L—G—E—R''   II wherein L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

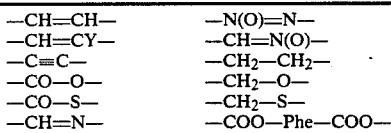

| —CH=CH— | —N(O)=N— |
| —CH=CY— | —CH=N(O)— |
| —C≡C— | —CH₂—CH₂— |
| —CO—O— | —CH₂—O— |
| —CO—S— | —CH₂—S— |
| —CH=N— | —COO—Phe—COO— | or a C—C single bond, Y is halogen, preferably chlorine, or —CN, and R' and R'' are alkyl, alkoxy, alkanoyloxy or alkoxycarbonyloxy with up to 18, preferably up to 8, carbon atoms, or one of these radicals is also CN, NC, NO₂, CF₃, F, Cl or Br.

In most of these compounds, R' and R'' differ, one of these radicals usually being an alkyl or alkoxy group. However, other variants of the envisaged substituents can also be used. Many such substances or mixtures thereof are commercially available. All of these substances can be prepared by methods which are known from the literature.

The phases according to the invention contain about 0.1 to 99%, preferably 10 to 95%, of one or more compounds of the formula I.

Dielectrics according to the invention containing 0.1 to 40%, preferably 0.5 to 30%, of one or more compounds of the formula I are also preferred.

The dielectrics according to the invention are prepared in a manner which is customary per se. As a rule, the components are dissolved in one another, advantageously at elevated temperature.

The liquid crystal dielectrics according to the invention can be modified by suitable additives so that they can be used in all the types of liquid crystal display elements which have hitherto been disclosed.

Such additives are known to the expert and are described in detail in the literature. For example, it is possible to add conductive salts, preferably ethyl-dimethyl-dodecyl-ammonium 4-hexyloxybenzoate, tetrabutylammonium tetraphenylboronate or complex salts of crown ethers (compare, for example, I. Haller et al., Mol. Cryst. Liq. Cryst. Volume 24, pages 249–258 (1973)), to improve the conductivity, dichroic dyestuffs, for the preparation of colored guest-host systems, or substances for modifying the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, M.p. is the melting point and C.p. is the clear point of a liquid crystal substance.

"Customary working-up" means: water is added, the mixture is extracted with methylene chloride, the organic phase is separated off, dried and evaporated and the product is purified by crystallization and/or chromatography.

EXAMPLE 1

1-(p-Bromophenyl)-2-(trans-4-n-pentylcyclohexyl)-ethane [obtainable by Friedel-Crafts acylation of benzene with trans-4-n-pentylcyclohexylacetyl chloride, Wolff-Kishner reduction of the carbonyl group and bromination of the aromatic in the p-position] is subjected to a Grignard reaction with 4-(4,5-dihydro-4,4-dimethyl-2-oxazolyl)-cyclohexanone. Detachment of water, with simultaneous removal of the oxazolyl protective group, by boiling with ethanolic H₂SO₄, hydrogenation of the double bond, conversion of the ethyl ester into the amide, dehydration analogously to Example 2 and customary working up gives 1-[p-(trans-4-cyanocyclohexyl)-phenyl]-2-(trans-4-n-pentylcyclohexyl)-ethane.

The following compounds are prepared analogously:

1-[p-(trans-4-cyanocyclohexyl)-phenyl]-2-(trans-4-ethylcyclohexyl)-ethane
1-[p-(trans-4-cyanocyclohexyl)-phenyl]-2-(trans-4-propylcyclohexyl)-ethane
1-[p-(trans-4-cyanocyclohexyl)-phenyl]-2-(trans-4-butylcyclohexyl)-ethane
1-[p-(trans-4-cyanocyclohexyl)-phenyl]-2-(trans-4-heptylcyclohexyl)-ethane
1-[4-(trans-4-cyanocyclohexyl)-3-fluorophenyl]-2-(trans-4-ethylcyclohexyl)-ethane
1-[4-(trans-4-cyanocyclohexyl)-3-fluorophenyl]-2-(trans-4-propylcyclohexyl)-ethane
1-[4-(trans-4-cyanocyclohexyl)-3-fluorophenyl]-2-(trans-4-butylcyclohexyl)-ethane
1-[4-(trans-4-cyanocyclohexyl)-3-fluorophenyl]-2-(trans-4-pentylcyclohexyl)-ethane
1-[4-(trans-4-cyanocyclohexyl)-3-fluorophenyl]-2-(trans-4-heptylcyclohexyl)-ethane.

EXAMPLE 2

36.7 g of 1-[4-(trans-4-n-propylcyclohexyl)-phenyl]-2-(4-carbamoyl-3-fluorophenyl)-ethane are suspended in 200 ml of methylene chloride and, after addition of 20 g of thionyl chloride and 3.5 ml of dimethylformamide, the mixture is boiled for 4 hours. After cooling, 500 ml of ice-water are added, the organic phase is separated off and worked up in the customary manner. After recrystallization from methanol, 18.1 g (52%) of 1-[4-(trans-4-n-propylcyclohexyl)-phenyl]-2-(4-cyano-3-fluorophenyl)-ethane are obtained.

The following compounds are prepared analogously:
1-[p-(trans-4-ethylcyclohexyl)-phenyl]-2-(4-cyano-3-fluorophenyl)-ethane
1-[p-(trans-4-butylcyclohexyl)-phenyl]-2-(4-cyano-3-fluorophenyl)-ethane
1-[p-(trans-4-pentylcyclohexyl)-phenyl]-2-(4-cyano-3-fluorophenyl)-ethane
1-[p-(trans-4-heptylcyclohexyl)-phenyl]-2-(4-cyano-3-fluorophenyl)-ethane
1[p-(trans-4-ethylcyclohexyl)-phenyl]-2-(4-cyano-3-methylphenyl)-ethane
1-[p-(trans-4-propylcyclohexyl)-phenyl]-2-(4-cyano-3-methylphenyl)-ethane
1-[p-(trans-4-butylcyclohexyl)-phenyl]-2-(4-cyano-3-methylphenyl)-ethane
1-[p-(trans-4-pentylcyclohexyl)-phenyl]-2-(4-cyano-3-methylphenyl)-ethane
1-[p-(trans-4-heptylcyclohexyl)-phenyl]-2-(4-cyano-3-methylphenyl)-ethane
1-[p-(trans-4-ethylcyclohexyl)-phenyl]-2-(4-cyano-2-fluorophenyl)-ethane
1-[p-(trans-4-propylcyclohexyl)-phenyl]-2-(4-cyano-2-fluorophenyl)-ethane
1-[p-(trans-4-butylcyclohexyl)-phenyl]-2-(4-cyano-2-fluorophenyl)-ethane
1-[p-(trans-4-pentylcyclohexyl)-phenyl]-2-(4-cyano-2-fluorophenyl)-ethane
1-[p-(trans-4-heptylcyclohexyl)-phenyl]-2-(4-cyano-2-fluorophenyl)-ethane
1-[4-(trans-4-ethylcyclohexyl)-2-fluorophenyl]-2-(4-cyanophenyl)-ethane
1-[4-(trans-4-propylcyclohexyl)-2-fluorophenyl]-2-(4-cyanophenyl)-ethane
1-[4-(trans-4-butylcyclohexyl)-2-fluorophenyl]-2-(4-cyanophenyl)-ethane
1-[4-(trans-4-pentylcyclohexyl)-2-fluorophenyl]-2-(4-cyanophenyl)-ethane
1-[4-(trans-4-heptylcyclohexyl)-2-fluorophenyl]-2-(4-cyanophenyl)-ethane
1-[4-(trans-4-ethylcyclohexyl-3-fluorophenyl]-2-(4-cyanophenyl)-ethane
1-[4-(trans-4-propylcyclohexyl-3-fluorophenyl]-2-(4-cyanophenyl)-ethane
1-[4-(trans-4-butylcyclohexyl-3-fluorophenyl]-2-(4-cyanophenyl)-ethane
1-[4-(trans-4-pentylcyclohexyl)-3-fluorophenyl]-2-(4-cyanophenyl)-ethane
1-[4-(trans-4-heptylcyclohexyl)-3-fluorophenyl]-2-(4-cyanophenyl)-ethane
1-[4-(trans-4-ethylcyclohexyl)-2-methylphenyl]-2-(4-cyanophenyl)-ethane
1-[4-(trans-4-propylcyclohexyl)-2-methylphenyl]-2-(4-cyanophenyl)-ethane
1-[4-(trans-4-butylcyclohexyl)-2-methylphenyl]-2-(4-cyanophenyl)-ethane
1-[4-(trans-4-pentylcyclohexyl)-2-methylphenyl]-2-(4-cyanophenyl)-ethane
1-[4-(trans-4-heptylcyclohexyl)-2-methylphenyl]-2-(4-cyanophenyl)-ethane
1-[4-(trans-4-ethylcyclohexyl)-2-chlorophenyl]-2-(4-cyanophenyl)-ethane
1-[4-(trans-4-propylcyclohexyl)-2-chlorophenyl]-2-(4-cyanophenyl)-ethane
1-[4-(trans-4-butylcyclohexyl)-2-chlorophenyl]-2-(4-cyanophenyl)-ethane
1-[4-(trans-4-pentylcyclohexyl)-2-chlorophenyl]-2-(4-cyanophenyl)-ethane
1-[4-(trans-4-heptylcyclohexyl)-2-chlorophenyl]-2-(4-cyanophenyl)-ethane.

EXAMPLE 3

A mixture of 38.4 g of 1-(trans-4-n-propylcyclohexyl)-2-(4'-bromo-2'-fluorobiphenyl-4-yl)-ethane (M.p. 61.1°, C.p. 114.7°), 10 g of $Cu_2(CN)_2$, 120 ml of pyridine and 60 ml of N-methylpyrrolidone is heated at 160° for 2 hours. The mixture is cooled, a solution of 120 g of $FeCl_3.6H_2O$ in 600 ml of 20% hydrochloric acid is added and the mixture is warmed at 70° for 1.5 hours, with stirring, and worked up in the customary manner to give 1-(trans-4-n-propylcyclohexyl)-2-(4'-cyano-2'-fluorobiphenyl-4-yl)-ethane, M.p. 89.4°, C.p. 168.4°.

EXAMPLE 4

1-(trans-4-n-Pentylcyclohexyl)-2-(4'-cyano-2'-fluorobiphenyl-4-yl)-ethane, M.p. 76.0°, C.p. 165.6°, is obtained analogously to Example 3 from 1-(trans-4-n-pentylcyclohexyl)-2-(4'-bromo-2'-fluorobiphenyl-4-yl)-ethane (M.p. 57.5°, C.p. 113.7°).

EXAMPLE 5

1-(trans-4-n-Heptylcyclohexyl)-2-(4'-cyano-2'-fluorobiphenyl-4-yl)-ethane, M.p. 74.5°, C.p. 157.4°, $S_A/N$ 108.0°, is obtained analogously to Example 3 from 1-(trans-4-n-heptylcyclohexyl)-2-(4'-bromo-2'-fluorobiphenyl-4-yl)-ethane (M.p. 54.0°, C.p. 113.0°).

The following compounds are prepared analogously:
1-(trans-4-methylcyclohexyl)-2-(4'-cyano-2'-fluorobiphenyl-4-yl)-ethane
1-(trans-4-ethylcyclohexyl)-2-(4'-cyano-2'-fluorobiphenyl-4-yl)-ethane
1-(trans-4-butylcyclohexyl)-2-(4'-cyano-2'-fluorobiphenyl-4-yl)-ethane
1-(trans-4-octylcyclohexyl)-2-(4'-cyano-2'-fluorobiphenyl-4-yl)-ethane 1-(trans-4-nonylcyclohexyl)-2-(4'-cyano-2'-fluorobiphenyl-4-yl)-ethane
1-(trans-4-decylcyclohexyl)-2-(4'-cyano-2'-fluorobiphenyl-4-yl)-ethane
1-(trans-4-methylcyclohexyl)-2-(4'-cyano-2-fluorobiphenyl-4-yl)-ethane
1-(trans-4-ethylcyclohexyl)-2-(4'-cyano-2-fluorobiphenyl-4-yl)-ethane
1-(trans-4-propylcyclohexyl)-2-(4'-cyano-2-fluorobiphenyl-4-yl)-ethane, M.p. 65.4°, C.p. 161.3°,
1-(trans-4-butylcyclohexyl)-2-(4'-cyano-2-fluorobiphenyl-4-yl)-ethane
1-(trans-4-pentylcyclohexyl)-2-(4'-cyano-2-fluorobiphenyl-4-yl)-ethane, M.p. 71.4°, C.p. 157.3°
1-(trans-4-heptylcyclohexyl)-2-(4'-cyano-2-fluorobiphenyl-4-yl)-ethane, M.p. 72.9°, C.p. 149.5°
1-(trans-4-octylcyclohexyl)-2-(4'-cyano-2-fluorobiphenyl-4-yl)-ethane
1-(trans-4-nonylcyclohexyl)-2-(4'-cyano-2-fluorobiphenyl-4-yl)-ethane
1-(trans-4-decylcyclohexyl)-2-(4'-cyano-2-fluorobiphenyl-4-yl)-ethane
1-(trans-4-ethylcyclohexyl)-2-(4'-cyano-2-methylbiphenyl-4-yl)-ethane
1-(trans-4-propylcyclohexyl)-2-(4'-cyano-2-methylbiphenyl-4-yl)-ethane
1-(trans-4-butylcyclohexyl)-2-(4'-cyano-2-methylbiphenyl-4-yl)-ethane
1-(trans-4-pentylcyclohexyl)-2-(4'-cyano-2-methylbiphenyl-4-yl)-ethane
1-(trans-4-heptylcyclohexyl)-2-(4'-cyano-2-methylbiphenyl-4-yl)-ethane.

EXAMPLE 6

A mixture of 43.0 g of 1-(trans-4-n-pentylcyclohexyl)-2-(4'-bromo-3'-fluorobiphenyl-4-yl)-ethane (M.p. 62.3°, C.p. 123.2°), 10 g of Cu$_2$(CN)$_2$, 120 ml of pyridine and 60 ml of N-methylpyrrolidone is heated at 160° for 2 hours and further processed analogously to Example 3. 1-(trans-4-n-Pentylcyclohexyl)-2-4'-cyano-3'-fluorobiphenyl-4-yl)-ethane, M.p. 58.5°, C.p. 149.7°, is obtained.

The following compounds are prepared analogously:
1-(trans-4-methylcyclohexyl)-2-(4'-cyano-3'-fluorobiphenyl-4-yl)-ethane
1-(trans-4-ethylcyclohexyl)-2-(4'-cyano-3'-fluorobiphenyl-4-yl)-ethane
1-(trans-4-propylcyclohexyl)-2-(4'-cyano-3'-fluorobiphenyl-4-yl)-ethane
1-(trans-4-butylcyclohexyl)-2-(4'-cyano-3'-fluorobiphenyl-4-yl)-ethane
1-(trans-4-heptylcyclohexyl)-2-(4'-cyano-3'-fluorobiphenyl-4-yl)-ethane
1-(trans-4-octylcyclohexyl)-2-(4'-cyano-3'-fluorobiphenyl-4-yl)-ethane
1-(trans-4-nonylcyclohexyl)-2-(4'-cyano-3'-fluorobiphenyl-4-yl)-ethane
1-(trans-4-decylcyclohexyl)-2-(4'-cyano-3'-fluorobiphenyl-4-yl)-ethane
1-[4-(trans-4-ethylcyclohexyl)-phenyl]-2-(4'-cyano-2-fluorobiphenyl-4-yl)-ethane
1-[4-(trans-4-propylcyclohexyl)-phenyl]-2-(4'-cyano-2-fluorobiphenyl-4-yl)-ethane
1-[4-(trans-4-butylcyclohexyl)-phenyl]-2-(4'-cyano-2-fluorobiphenyl-4-yl)-ethane
1-[4-(trans-4-pentylcyclohexyl)-phenyl]-2-(4'-cyano-2-fluorobiphenyl-4-yl)-ethane
1-[4-(trans-4-heptylcyclohexyl)-phenyl]-2-(4'-cyano-2-fluorobiphenyl-4-yl)-ethane
1-[4-(trans-4-ethylcyclohexyl)-phenyl]-2-(4'-cyano-2'-fluorobiphenyl-4-yl)-ethane
1-[4-(trans-4-propylcyclohexyl)-phenyl]-2-(4'-cyano-2'-fluorobiphenyl-4-yl)-ethane
1-[4-(trans-4-butylcyclohexyl)-phenyl]-2-(4'-cyano-2'-fluorobiphenyl-4-yl)-ethane
1-[4-(trans-4-pentylcyclohexyl)-phenyl]-2-(4'-cyano-2'-fluorobiphenyl-4-yl)-ethane
1-[4-(trans-4-heptylcyclohexyl)-phenyl]-2-(4'-cyano-2'-fluorobiphenyl-4-yl)-ethane
1-[4-(trans-4-ethylcyclohexyl)-phenyl]-2-(4'-cyano-2'-chlorobiphenyl-4-yl)-ethane
1-[4-(trans-4-propylcyclohexyl)-phenyl]-2-(4'-cyano-2'-chlorobiphenyl-4-yl)-ethane
1-[4-(trans-4-butylcyclohexyl)-phenyl]-2-(4'-cyano-2'-chlorobiphenyl-4-yl)-ethane
1-[4-(trans-4-pentylcyclohexyl)-phenyl]-2-(4'-cyano-2'-chlorobiphenyl-4-yl)-ethane
1-[4-(trans-4-heptylcyclohexyl)-phenyl]-2-(4'-cyano-2'-chlorobiphenyl-4-yl)-ethane
1-[4-(trans-4-ethylcyclohexyl)-phenyl]-2-(4'-cyano-2'-methylbiphenyl-4-yl)-ethane
1-[4-(trans-4-propylcyclohexyl)-phenyl]-2-(4'-cyano-2'-methylbiphenyl-4-yl)-ethane
1-[4-(trans-4-butylcyclohexyl)-phenyl]-2-(4'-cyano-2'-methylbiphenyl-4-yl)-ethane
1-[4-(trans-4-pentylcyclohexyl)-phenyl]-2-(4'-cyano-2'-methylbiphenyl-4-yl)-ethane
1-[4-(trans-4-heptylcyclohexyl)-phenyl]-2-(4'-cyano-2'-methylbiphenyl-4-yl)-ethane
1-(trans, trans-4-ethylbicyclohex-4'-yl)-2-(4'-cyano-2-fluorobiphenyl-4-yl)-ethane
1-(trans, trans-4-propylbicyclohex-4'-yl)-2-(4'-cyano-2-fluorobiphenyl-4-yl)-ethane
1-(trans, trans-4-butylbicyclohex-4'-yl)-2-(4'-cyano-2-fluorobiphenyl-4-yl)-ethane
1-(trans, trans-4-pentylbicyclohex-4'-yl)-2-(4'-cyano-2-fluorobiphenyl-4-yl)-ethane
1-(trans, trans-4-heptylbicyclohex-4'-yl)-2-(4'-cyano-2-fluorobiphenyl-4-yl)-ethane
1-(trans, trans-4-ethylbicyclohex-4'-yl)-2-(4'-cyano-2'-fluorobiphenyl-4-yl)-ethane
1-(trans, trans-4-propylbicyclohex-4'-yl)-2-(4'-cyano-2'-fluorobiphenyl-4-yl)-ethane
1-(trans, trans-4-butylbicyclohex-4'-yl)-2-(4'-cyano-2'-fluorobiphenyl-4-yl)-ethane
1-(trans, trans-4-pentylbicyclohex-4'-yl)-2-(4'-cyano-2'-fluorobiphenyl-4-yl)-ethane
1-(trans, trans-4-heptylbicyclohex-4'-yl)-2-(4'-cyano-2'-fluorobiphenyl-4-yl)-ethane
1-(trans, trans-4-ethylbicyclohex-4'-yl)-2-(4'-cyano-2'-chlorobiphenyl-4-yl)-ethane
1-(trans, trans-4-propylbicyclohex-4'-yl)-2-(4'-cyano-2'-chlorobiphenyl-4-yl)-ethane
1-(trans, trans-4-butylbicyclohex-4'-yl)-2-(4'-cyano-2'-chlorobiphenyl-4-yl)-ethane
1-(trans, trans-4-pentylbicyclohex-4'-yl)-2-(4'-cyano-2'-chlorobiphenyl-4-yl)-ethane
1-(trans, trans-4-heptylbicyclohex-4'-yl)-2-(4'-cyano-2'-chlorobiphenyl-4-yl)-ethane
1-(trans, trans-4-ethylbicyclohex-4'-yl)-2-(4'-cyano-2'-methylbiphenyl-4-yl)-ethane
1-(trans, trans-4-propylbicyclohex-4'-yl)-2-(4'-cyano-2'-methylbiphenyl-4-yl)-ethane
1-(trans, trans-4-butylbicyclohex-4'-yl)-2-(4'-cyano-2'-methylbiphenyl-4-yl)-ethane 1-(trans, trans-4-pentylbicyclohex-4'-yl)-2-(4'-cyano-2'-methylbiphenyl-4yl)-ethane 1-(trans, trans-4-heptylbicyclohex-4'-yl)-2-(4'-cyano-2'-methylbiphenyl-4-yl)-ethane.

EXAMPLE 7

A mixture of 3.6 g of (trans-4-n-pentylcyclohexyl)ethylmalondialdehyde bis-diethyl acetal and 2.1 g of the carboximide-amide of ethyl 4-cyano-2-fluoro-benzoate is heated at 145° for 20 hours. After cooling, the residue is dissolved in ethanol, the solution is worked up in the customary manner and the resulting ester is converted into the nitrile in the customary manner. 2-(4-cyano-3-fluorophenyl)-5-[2-(trans-4-n-pentylcyclohexyl)-ethyl]-pyrimidine is obtained.

The following compounds are prepared analogously:

2-(4-cyano-3-fluorophenyl)-5-[2-(trans-4-ethylcyclohexyl)-ethyl]-pyrimidine 2-(4-cyano-3-fluorophenyl)-5-[2-(trans-4-propylcyclohexyl)-ethyl]-pyrimidine 2-(4-cyano-3-fluorophenyl)-5-[2-(trans-4-butylcyclohexyl)-ethyl]-pyrimidine 2-(4-cyano-3-fluorophenyl)-5-[2-(trans-4-heptylcyclohexyl)-ethyl]-pyrimidine 2-(4-cyano-3-methylphenyl)-5-[2-(trans-4-ethylcyclohexyl)-ethyl]-pyrimidine 2-(4-cyano-3-methylphenyl)-5-[2-(trans-4-propylcyclohexyl)-ethyl]-pyrimidine 2-(4-cyano-3-methylphenyl)-5-[2-(trans-4-butylcyclohexyl)-ethyl]-pyrimidine 2-(4-cyano-3-methylphenyl)-5-[2-(trans-4-pentylcyclohexyl)-ethyl]-pyrimidine 2-(4-cyano-3-methylphenyl)-5-[2-(trans-4-heptylcyclohexyl)-ethyl]-pyrimidine 2-(4-cyanophenyl)-3-fluoro-5-[2-(trans-4-ethylcyclohexyl)-ethyl]-pyrimidine 2-(4-cyanophenyl)-3-fluoro-5-[2-(trans-4-propylcyclohexyl)-ethyl]-pyrimidine 2-(4-cyanophenyl)-3-fluoro-5-[2-(trans-4-butylcyclohexyl)-ethyl]-pyrimidine 2-(4-cyanophenyl)-3-fluoro-5-[2-(trans-4-pentylcyclohexyl)-ethyl]-pyrimidine 2-(4-cyanophenyl)-3-fluoro-5-[2-(trans-4-heptylcyclohexyl)-ethyl]-pyrimidine 2-(4-cyanophenyl)-3-chloro-5-[2-(trans-4-ethylcyclohexyl)-ethyl]-pyrimidine 2-(4-cyanophenyl)-3-chloro-5-[2-(trans-4-propylcyclohexyl)ethyl]-pyrimidine 2-(4-cyanophenyl)-3-chloro-5-[2-(trans-4-butylcyclohexyl)ethyl]-pyrimidine 2-(4-cyanophenyl)-3-chloro-5-[2-(trans-4-pentylcyclohexyl)ethyl]pyrimidine 2-(4-cyanophenyl)-3-chloro-5-[2-(trans-4-heptylcyclohexyl)ethyl]-pyrimidine 2-(4-cyanophenyl)-5-[2-(trans-4-ethylcyclohexyl)-ethyl]-pyrimidine 2-(4-cyanophenyl)-5-[2-(trans-4-propylcyclohexyl)-ethyl]-pyrimidine 2-(4-cyanophenyl)-5-[2-(trans-4-butylcyclohexyl)-ethyl]-pyrimidine 2-(4-cyanophenyl)-5-[2-(trans-4-pentylcyclohexyl)-ethyl]-pyrimidine 2-(4-cyanophenyl)-5-[2-(trans-4-heptylcyclohexyl)-ethyl]-pyrimidine 2-(4-cyanophenyl)-5-[2-(trans-4-ethylcyclohexyl)-ethyl]-pyrazine 2-(4-cyanophenyl)-5-[2-(trans-4-propylcyclohexyl)-ethyl]-pyrazine 2-(4-cyanophenyl)-5-[2-(trans-4-butylcyclohexyl)-ethyl]-pyrazine 2-(4-cyanophenyl)-5-[2-(trans-4-pentylcyclohexyl)-ethyl]-pyrazine 2-(4-cyanophenyl)-5-[2-(trans-4-heptylcyclohexyl)-ethyl]-pyrazine.

The following examples relate to liquid crystal phases according to the invention:

EXAMPLE A

A mixture is prepared from

15% of p-trans-4-propylcyclohexyl-benzonitrile,

27% of trans-1-p-ethylphenyl-4-propylcyclohexane,

10% of trans-2-p-ethoxyphenyl-4-propylcyclohexane,

7% of 4-cyano-4'-(trans-4-pentylcyclohexyl)-bi-biphenyl,

10% of 4-(trans-4-pentylcyclohexyl)-4'-(trans-4-propylcyclohexyl)-biphenyl,

8% of p-propylphenyl p-trans-4-propylcyclohexylbenzoate,

6% of p-propylphenyl p-trans-4-pentylcyclohexylbenzoate and

17% of 2-(4-cyano-2-fluorophenyl)-5-[2-(trans-4-pentylcyclohexyl)-ethyl]-pyrimidine.

EXAMPLE B

A mixture is prepared from

15% of p-trans-4-propylcyclohexyl-benzonitrile,

12% of p-trans-4-butylcyclohexyl-benzonitrile,

14% of trans-1-p-ethylphenyl-4-propylcyclohexane,

10% of trans-1-p-ethoxyphenyl-4-propylcyclohexane,

6% of 4-cyano-4'-(trans-4-pentylcyclohexyl)-biphenyl,

4% of 4,4'-bis-(trans-4-propylcyclohexyl)-biphenyl,

6% of 4-(trans-4-pentylcyclohexyl)-4'-(trans-4-propylcyclohexyl)-biphenyl,

8% of p-propylphenyl p-trans-4-propylcyclohexylbenzoate,

16% of p-propylphenyl p-trans-4-pentylcyclohexylbenzoate and

9% of 1-[4-(4-trans-pentylcyclohexyl)-2-fluorophenyl]-2-(4-cyanophenyl)-ethane.

EXAMPLE C

A mixture is prepared from 19.0% of 4-(trans-4-n-propylcyclohexyl)-benzonitrile, 29.0% of 4-(trans-4-n-pentylcyclohexyl)-benzonitrile, 20.0% of 4-(trans-4-n-heptylcyclohexyl)-benzonitrile, 12.0% of trans-4-n-pentyl-(4'-cyanobiphenylyl-4)-cyclohexane, 8.5% of 4,4'-bis-(trans-4-propylcyclohexyl)-biphenyl, 11.0% of 2-p-cyanophenyl-4'-heptyl-1,3-dioxane and 0.5% of 1-[p-(4-trans-butylcyclohexyl)-phenyl]-2-(4-cyano-2-fluorophenyl)-ethane.

EXAMPLE D

A mixture is prepared from

19% of 4-(trans-4-n-propylcyclohexyl)-benzonitrile,

28% of 4-(trans-4-n-pentylcyclohexyl)-benzonitrile,

11% of trans-4-n-pentyl-(4'-cyanobiphenylyl-4)-cyclohexane,

10% of 4-propylphenyl 4-(trans-4-n-propylcyclohexyl)-benzoate,

12% of trans-4-n-propylcyclohexyl 4-(trans-4-n-propylcyclohexyl)-benzoate,

12% of 1-(4-trans-pentylcyclohexyl)-2-(4'-cyano-2'-fluorobiphenyl-4-yl)-ethane,

7% of 2-(4-cyanophenyl)-5-[2-(trans-4-pentylcyclohexyl)-ethyl]-pyrimidine and

1% of 1-[p-(4-trans-pentylcyclohexyl)-phenyl]-2-(4'-cyano-2-fluorobiphenyl-4-yl)-ethane.

EXAMPLE E

A mixture is prepared from
3% of 4-ethyl-4'-(trans-4-propylcyclohexyl)-biphenyl,
5% of 4-ethyl-4'-(trans-4-pentylcyclohexyl)-biphenyl,
5% of 2-p-pentyloxyphenyl-5-hexylpyrimidine,
5% of 2-p-hexyloxyphenyl-5-hexylpyrimidine,
6% of 2-p-heptyloxyphenyl-5-hexylpyrimidine,
8% of 2-p-nonyloxyphenyl-5-hexylpyrimidine,
8% of 2-p-undecyloxyphenyl-5-hexylpyrmidine,
7% of p-methoxyphenyl trans-4-propylcyclohexanecarboxylate,
5% p-methoxyphenyl trans-4-butylcyclohexanecarboxylate,
4% of p-methoxyphenyl trans-4-pentylcyclohexanecarboxylate,
18% of 2-(4-cyano-2-fluorophenyl)-5-[2-(trans-4-pentylcyclohexyl)-ethyl]-pyrimidine and
12% of 2-(4-cyanophenyl)-5-[2-(trans-4-propylcyclohexyl)-ethyl]-pyrimidine.
10% of trans-1-p-ethylphenyl-4-pentylcyclohexane and
4% of p-trans-4-propylcyclohexylphenyl butyrate.

This mixture is particularly suitable as a dielectric for liquid crystal display elements with a high multiplex ratio.

EXAMPLE F

A mixture is prepared from
15% of p-trans-4-propylcyclohexylbenzonitrile,
27% of trans-1-p-ethylphenyl-4-propylcyclohexane,
10% of trans-2-p-ethoxyphenyl-4-propylcyclohexane,
7% of 4-cyano-4'-(trans-4-pentylcyclohexyl)-biphenyl,
10% of 4-(trans-4-pentylcyclohexyl)-4'-(trans-4-propylcyclohexyl)-biphenyl,
8% of p-propylphenyl p-trans-4-propylcyclohexylbenzoate,
6% of p-propylphenyl p-trans-4-pentylcyclohexylbenzoate,
8% of 1-(trans-4-propylcyclohexyl)-2-(4'-cyano-2'-fluorobiphenyl-4-yl)-ethane,
5% of 1-(trans-4-pentylcyclohexyl)-2-(4'-cyano-2'-fluorobiphenyl-4-yl)-ethane and
4% of 1-(trans-4-heptylcyclohexyl)-2-(4'-cyano-2'-fluorobiphenyl-4-yl)-ethane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline phase comprising at least two liquid crystal components, the improvement wherein at least one liquid crystal component is an ethane derivative of the formula $$R^1-A^1-CH_2CH_2-A^2-(A^3)_n-R^2$$

wherein
$R^1$ is H; alkyl of 1–12 C atoms; alkyl of 1–12 C atoms in which one or two non-adjacent $CH_2$ groups are independently replaced by O, alkylcarbonyl of 1–12 c atoms; alkylcarbonyloxy of 1–12 c atoms; alkoxycarbonyl of 1–12 c atoms; F; Cl; or Br;
$R^2$ is —CN or —$Z^2$—$A^4$—CN,
$A^1$ is —A—, —A—$A^5$— or —$A^5$—A—,
$A^2$ is 1,4-phenylene; 1,4-phenylene substituted by one of F, Cl, $CH_3$, or CN; or 1,4-phenylene wherein two CH groups are replaced by N atoms,
A is 1,4-cyclohexylene or 1,4-bicyclo(2,2,2)-octylene,
$A^3$ and $A^4$ each independently is 1,4-cyclohexylene; 1,4-phenylene; 1,4-phenylene substituted by one of F, Cl, $CH_3$, or CN; or 1,4-phenylene wherein two CH groups are replaced by N atoms,
$A^5$ is 1,4-phenylene or 1,4-phenylene wherein two CH groups are replaced by N atoms,
n is 0 or 1,
$Z^2$ is —$CH_2CH_2$—, —$CH_2O$—, —$OCH_2$— or —O—CO— and
with the provisos that:
(a) at least one of the groups $A^2$ and $A^3$ is laterally substituted, and
(b) if $A^1$=A, or $R^1$—$A^1$=trans-4-(trans-4-alkylcyclohexyl)-cyclohexyl, n is 1.

2. A phase of claim 1 wherein said formula is $$R^1-A-A^5-CH_2CH_2-A^2-CN$$

$$R^1-A^5-A-CH_2CH_2-A^2-CN$$

or $$R^1-A-CH_2CH_2-A^2-A^3-CN.$$

3. A phase of claim 1 wherein said formula is $$R^1-A-CH_2CH_2-A^2-A^3-Z^2-A^4-CN$$

$$R^1-A-A^5-CH_2CH_2-A^2-A^3-CN$$

or $$R^1-A^5-A-CH_2CH_2-A^2-A^3-CN.$$

4. A phase of claim 1 wherein said formula is $$R^1-A-A^5-CH_2CH_2-A^2-A^3-Z^2-A^4-CN$$

or $$R^1-A^5-A-CH_2CH_2-A^2-A^3-Z^2-A^4-CN.$$

5. A phase of claim 1 wherein said formula is $$R^1-Cy-Phe-CH_2CH_2-PhX-CN$$

wherein Phe is 1,4-phenylene, Cy is 1,4-cyclohexylene, and PhX is Phe substituted by one of F, Cl, $CH_3$ or CN.

6. A phase of claim 1 wherein said formula is $$R^1-A-CH_2CH_2-Pyr-PhX-CN$$

$$R^1-A-CH_2CH_2-PhX-Phe-CN$$

$$R^1-A-CH_2CH_2-Phe-PhX-CN$$

or $$R^1-A-CH_2CH_2-PhX-Cy-CN$$

wherein Phe is 1,4-phenylene, Cy is 1,4-cyclohexylene, Pyr is pyrimidine-2,5-diyl and PhX is Phe substituted by one of F, Cl, CH₃ or CN.

7. A phase of claim 1 wherein said formula is

R¹—A—CH₂CH₂—PhX—Phe—Cy—CN or

R¹—A—CH₂CH₂—Phe—PhX—Cy—CN wherein Phe is 1,4-phenylene, Cy is 1,4-cyclohexylene and PhX is Phe substituted by one of F, Cl, CH₃ or CN.

8. A phase of claim 1 wherein said formula is

R¹—A—Phe—CH₂CH₂—PhX—Phe—CN

R¹—A—Phe—CH₂CH₂—Phe—PhX—CN

R¹—A—Phe—CH₂CH₂—Phe—PhX—CN or

R¹—A—Phe—CH₂CH₂—PhX—Cy—CN wherein Phe is 1,4-phenylene, Cy is 1,4-cyclohexylene and PhX is Phe substituted by one of F, Cl, CH₃ or CN.

9. A phase of claim 1 wherein said formula is

R¹—Cy—A—CH₂CH₂—PhX—Phe—CN

R¹—Cy—A—CH₂CH₂—Phe—PhX—CN or

R¹—Cy—A—CH₂CH₂—PhX—Cy—CN wherein Phe is 1,4-phenylene, Cy is 1,4-cyclohexylene and PhX is Phe substituted by one of F, Cl, CH₃ or CN.

10. A phase of claim 1 wherein in said formula R¹ is alkyl, alkoxy or oxa-containing alkyl.

11. A phase of claim 1 wherein in said formula

A¹ is —A— or —A—A⁵—.

12. A phase of claim 1 wherein in said formula, A is 1,4-cyclohexylene.

13. A phase of claim 1 wherein in said formula A² is Phe, PhX, Pyr, or Pyn wherein Phe is 1,4-phenylene, Pyn is pyridazine-3,6-diyl, Pyr is pyrimidine-2,5-diyl and PhX is Phe substituted in the 2- or 3-position by F, Cl or CH₃.

14. A phase of claim 1 wherein in said formula A³ and A⁴ and A⁵ each independently is Phe, PhX, or Cy wherein Phe is 1,4-phenylene, Cy is 1,4-cyclohexylene, and PhX is Phe substituted in the 2- or 3-position by F, Cl or CH₃.

15. A phase of claim 1 wherein Z¹ and Z² is a single bond.

16. In a liquid crystal display element, comprising a liquid crystal phase, the improvement wherein the phase is one of claim 1.

17. In a liquid crystal electro-optical display element, comprising a liquid crystal dielectric, the improvement wherein the dielectric is a phase of claim 1.

18. A phase of claim 1, wherein A is 1,4-bicyclo(2,2,2)-octylene.

19. A phase according to claim 1, wherein only one of the groups A² and A³ is laterally substituted.

20. A phrase according to claim 1, wherein said phase comprises a laterally fluorinated ethane derivative.

* * * * *